(12) United States Patent
Weber et al.

(10) Patent No.: US 12,029,603 B2
(45) Date of Patent: Jul. 9, 2024

(54) SYSTEM AND METHOD FOR PROVIDING IMAGING PARAMETERS

(71) Applicant: DÜRR DENTAL SE, Bietigheim-Bissingen (DE)

(72) Inventors: Michael Weber, Burgstetten (DE); Bernd Philipps, Untergruppenbach (DE)

(73) Assignee: DÜRR DENTAL SE, Bietigheim-Bissingen (DE)

( * ) Notice: Subject to any disclaimer, the term of this patent is extended or adjusted under 35 U.S.C. 154(b) by 495 days.

(21) Appl. No.: 16/332,445

(22) PCT Filed: Sep. 12, 2017

(86) PCT No.: PCT/EP2017/072839
§ 371 (c)(1),
(2) Date: Mar. 12, 2019

(87) PCT Pub. No.: WO2018/046749
PCT Pub. Date: Mar. 15, 2018

(65) Prior Publication Data
US 2021/0282729 A1    Sep. 16, 2021

(30) Foreign Application Priority Data
Sep. 12, 2016 (DE) .................. 10 2016 117 051.8

(51) Int. Cl.
*A61B 6/00* (2006.01)
*A61B 6/14* (2006.01)
(Continued)

(52) U.S. Cl.
CPC .......... *A61B 6/5294* (2013.01); *A61B 6/4216* (2013.01); *A61B 6/425* (2013.01);
(Continued)

(58) Field of Classification Search
CPC .. A61B 6/14; A61B 6/145; A61B 6/42; A61B 6/4208; A61B 6/4216; A61B 6/425;
(Continued)

(56) References Cited

U.S. PATENT DOCUMENTS 4,498,005 A * 2/1985 Oono ................... A61B 6/4494
250/484.4
4,498,006 A    2/1985 Horikawa
(Continued)

FOREIGN PATENT DOCUMENTS

CN    18 46 216 A    10/2006
CN    19 91 575 A    7/2007
(Continued)

OTHER PUBLICATIONS

Unpublished U.S. Appl. No. 16/332,456, filed Mar. 12, 2019.
(Continued)

*Primary Examiner* — Allen C. Ho
(74) *Attorney, Agent, or Firm* — Chiesa Shahinian & Giantomasi PC

(57) ABSTRACT

A system having an X-ray imaging device for capturing an X-ray image on an imaging film, and a device for reading out the imaging film. The imaging film includes a data carrier, and the X-ray imaging device and/or the readout device includes a data device that has a write/read device for writing, on the data carrier, imaging parameters relating to the X-ray image capture and for reading information that is stored on the data carrier, the write/read device being configured to transmit the read information to the readout device such that the imaging parameters in force when capturing the X-ray image are available to the readout device for an imaging film readout. A method for providing information for a readout device is also provided.

10 Claims, 4 Drawing Sheets

(51) Int. Cl.
| | |
|---|---|
| *A61B 6/42* | (2024.01) |
| *A61B 6/46* | (2024.01) |
| *A61B 6/51* | (2024.01) |
| *G01T 1/20* | (2006.01) |
| *G06K 19/06* | (2006.01) |
| *H04N 5/32* | (2023.01) |

(52) U.S. Cl.
CPC .......... *A61B 6/4452* (2013.01); *A61B 6/4458* (2013.01); *A61B 6/4494* (2013.01); *A61B 6/468* (2013.01); *A61B 6/512* (2024.01); *A61B 6/52* (2013.01); *G01T 1/2012* (2013.01); *G01T 1/2014* (2013.01); *G06K 19/06028* (2013.01); *H04N 5/32* (2013.01); *A61B 6/51* (2024.01)

(58) Field of Classification Search
CPC ....... A61B 6/44; A61B 6/4452; A61B 6/4458; A61B 6/4494; A61B 6/52; A61B 6/5205; A61B 6/5211; A61B 6/5294; A61B 6/54; A61B 6/542; A61B 6/544; A61B 6/545; A61B 6/467; A61B 6/468
USPC .............. 378/38–40, 62, 162–166, 168–170, 378/167–188; 250/580–591
See application file for complete search history.

(56) References Cited

U.S. PATENT DOCUMENTS

| | | | | |
|---|---|---|---|---|
| 4,672,184 A * | 6/1987 | Fujiwara | ............ | G06K 7/10861 235/462.43 |
| 4,783,588 A * | 11/1988 | Schmidt | ............... | G03B 42/045 250/580 |
| 4,791,282 A * | 12/1988 | Schmidt | ............... | G03B 42/045 235/475 |
| 5,027,380 A | 6/1991 | Nishiki | | |
| 5,148,464 A * | 9/1992 | Metoki | ................ | G03B 42/047 378/162 |
| 5,195,123 A * | 3/1993 | Clement | ............... | G03B 42/047 378/165 |
| 5,231,656 A * | 7/1993 | Sakuma | ................ | G03B 27/521 378/177 |
| 5,264,684 A | 11/1993 | Weil | | |
| 5,288,977 A * | 2/1994 | Amendolia | .......... | G03B 42/047 235/375 |
| 5,376,806 A | 12/1994 | Hejazi | | |
| 5,377,253 A * | 12/1994 | Ifuku | ..................... | A61B 6/487 378/98.2 |
| 5,420,441 A * | 5/1995 | Newman | ................ | G01T 1/2014 250/252.1 |
| 5,515,137 A * | 5/1996 | Arnold | ................. | G03B 42/045 378/166 |
| 5,592,374 A * | 1/1997 | Fellegara | ................ | G16H 30/20 705/28 |
| 5,596,202 A | 1/1997 | Arakawa | | |
| 5,627,381 A * | 5/1997 | Kulpinski | .............. | G03B 42/02 250/588 |
| 5,757,021 A | 5/1998 | Dewaele | | |
| 5,865,745 A * | 2/1999 | Schmitt | ................ | G03B 42/047 250/580 |
| 6,047,257 A * | 4/2000 | Dewaele | ................. | A61B 6/4494 704/E15.044 |
| 6,271,536 B1 * | 8/2001 | Buytaert | ............ | G03B 42/042 250/584 |
| 6,359,628 B1 * | 3/2002 | Buytaert | ............ | G03B 42/047 345/619 |
| 6,381,416 B2 * | 4/2002 | Manico | .................. | B65H 1/266 396/207 |
| 6,431,440 B1 * | 8/2002 | Tsuchino | ................ | G03B 42/08 235/462.13 |
| 6,710,891 B1 * | 3/2004 | Vraa | ...................... | G03B 42/04 235/385 |
| 6,771,355 B2 * | 8/2004 | Ishii | ........................ | G03C 3/00 378/182 |
| 7,083,106 B2 | 8/2006 | Albany | | |
| 7,092,970 B2 * | 8/2006 | Shiibashi | ............. | A61B 6/4494 |
| 7,095,034 B2 * | 8/2006 | Haug | .................... | G01T 1/2014 250/483.1 |
| 7,103,140 B2 * | 9/2006 | Amitani | ............... | A61B 6/4233 378/53 |
| 7,162,067 B2 * | 1/2007 | Motoki | .................. | G16H 30/20 378/165 |
| 7,180,042 B2 * | 2/2007 | Ito | ......................... | A61B 6/583 250/587 |
| 7,244,955 B2 | 7/2007 | Bueno et al. | | |
| 7,319,396 B2 * | 1/2008 | Homanfar | ............. | A61B 6/14 340/572.1 |
| 7,355,195 B2 | 4/2008 | Ivo | | |
| 7,395,974 B2 | 7/2008 | Albany | | |
| 7,397,058 B2 * | 7/2008 | Struble | ............... | G03B 42/047 250/584 |
| 7,550,754 B2 | 6/2009 | Bueno et al. | | |
| 7,556,426 B2 * | 7/2009 | Nakajo | ................. | G03B 42/04 378/188 |
| 7,561,668 B2 * | 7/2009 | Ohta | ...................... | G03B 42/04 378/102 |
| 7,573,034 B2 * | 8/2009 | Heath | ..................... | G03B 42/02 250/361 R |
| 7,620,230 B2 * | 11/2009 | Haug | ..................... | G03B 42/04 250/584 |
| 7,628,537 B2 * | 12/2009 | Schulze-Ganzlin | ... | A61B 6/145 378/170 |
| 7,787,587 B2 * | 8/2010 | Tasaki | .................... | A61B 6/542 378/98.7 |
| 7,793,848 B2 | 9/2010 | Abe et al. | | |
| 7,896,229 B2 * | 3/2011 | Crucs | ..................... | A61B 6/00 235/375 |
| 7,944,478 B2 * | 5/2011 | Shiibashi | ............... | G16H 30/20 348/222.1 |
| 8,265,369 B2 * | 9/2012 | Crucs | ................... | A61B 6/4216 382/132 |
| 8,374,461 B2 * | 2/2013 | Humphreys | ............ | A61B 6/40 382/128 |
| 8,693,748 B2 * | 4/2014 | Jouhikainen | ........... | G06V 10/24 382/128 |
| 8,833,647 B2 * | 9/2014 | Berger | .................. | A61B 90/90 235/492 |
| 8,838,207 B2 * | 9/2014 | Nakayama | ............. | A61B 6/469 600/568 |
| 8,866,096 B2 * | 10/2014 | Eguchi | ..................... | A61B 6/00 250/370.11 |
| 9,066,648 B2 * | 6/2015 | Kyllonen | ............ | G06K 7/10366 |
| 9,211,102 B2 * | 12/2015 | Taskinen | ................ | A61B 6/14 |
| 9,245,161 B2 | 1/2016 | Berger et al. | | |
| 9,339,246 B2 * | 5/2016 | Lemaire | ................ | A61B 6/545 |
| 9,351,690 B2 * | 5/2016 | Nachaliel | ............... | A61B 6/547 |
| 9,384,864 B2 * | 7/2016 | Nelson | ................. | A61B 6/4494 |
| 9,405,183 B2 * | 8/2016 | Ando | .................... | G03B 42/02 |
| 9,626,613 B2 * | 4/2017 | Berger | .................. | H04B 5/0025 |
| 9,678,420 B2 * | 6/2017 | Taskinen | ................ | A61B 6/547 |
| 9,955,933 B2 | 5/2018 | Taskinen et al. | | |
| 10,139,497 B2 | 11/2018 | Philipps et al. | | |
| 10,393,889 B2 | 8/2019 | Philipps et al. | | |
| 10,591,615 B2 | 3/2020 | Philipps et al. | | |
| 10,722,198 B2 * | 7/2020 | Wirth | ................... | A61B 6/4494 |
| 10,835,195 B2 | 11/2020 | Taskinen et al. | | |
| 11,337,662 B2 * | 5/2022 | Varlet | ................... | A61B 6/4452 |
| 11,737,720 B2 * | 8/2023 | Weber | ................... | G01T 1/2014 250/370.09 |
| 2005/0051614 A1 | 3/2005 | Albany | | |
| 2005/0133730 A1 | 6/2005 | Haug et al. | | |
| 2005/0134936 A1 | 6/2005 | Haug et al. | | |
| 2006/0219765 A1 | 10/2006 | Snyder | | |
| 2007/0138419 A1 | 6/2007 | Bueno et al. | | |
| 2008/0093462 A1 | 4/2008 | Abe et al. | | |
| 2008/0185535 A1 | 8/2008 | Bueno et al. | | |
| 2009/0212107 A1 | 8/2009 | Crucs et al. | | |
| 2010/0104065 A1 | 4/2010 | Eguchi | | |
| 2010/0185459 A1 | 7/2010 | Vera et al. | | |

(56) References Cited

U.S. PATENT DOCUMENTS

| | | |
|---|---|---|
| 2010/0266187 A1 | 10/2010 | Crucs |
| 2012/0001737 A1 | 1/2012 | Berger et al. |
| 2012/0019369 A1 | 1/2012 | Taskinen et al. |
| 2012/0181437 A1 | 7/2012 | Nelson et al. |
| 2014/0049380 A1 | 2/2014 | Berger et al. |
| 2014/0252252 A1 | 9/2014 | Philipps et al. |
| 2015/0324680 A1 | 11/2015 | Berger et al. |
| 2017/0238891 A1 | 8/2017 | Taskinen et al. |
| 2018/0214102 A1 | 8/2018 | Taskinen et al. |
| 2018/0354083 A1 | 12/2018 | Thorwarth |
| 2019/0049598 A1 | 2/2019 | Philipps et al. |
| 2019/0339401 A1 | 11/2019 | Philipps et al. |
| 2021/0085269 A1 | 3/2021 | Taskinen et al. |
| 2021/0282729 A1 | 9/2021 | Weber et al. |
| 2021/0286094 A1 | 9/2021 | Weber et al. |

FOREIGN PATENT DOCUMENTS

| | | |
|---|---|---|
| CN | 101 069 285 A | 11/2007 |
| CN | 101 797 159 A | 8/2010 |
| CN | 102 422 222 | 4/2012 |
| CN | 103 988 265 | 8/2014 |
| EP | 0 908 762 | 4/1999 |
| EP | 1 544 672 | 6/2005 |
| EP | 1 544 673 | 6/2005 |
| EP | 1 544 803 A2 | 6/2005 |
| EP | 2 386 904 | 11/2011 |
| EP | 3509496 A1 | 7/2019 |
| EP | 3509493 B1 | 2/2021 |
| JP | S5872041 A | 4/1983 |
| JP | S5883937 A | 5/1983 |
| JP | S6125530 A | 2/1986 |
| JP | H06202254 A | 7/1994 |
| JP | H0792584 A | 4/1995 |
| JP | H08-87085 | 4/1996 |
| JP | H11202433 A | 7/1999 |
| JP | 2000-284116 | 10/2000 |
| JP | 2003-210446 | 7/2003 |
| JP | 2006048072 A | 2/2006 |
| JP | 2006065347 A | 3/2006 |
| JP | 2011043977 A | 3/2011 |
| JP | 2011-251119 | 12/2011 |
| JP | 2012-521238 | 9/2012 |
| JP | 2015213754 A | 12/2015 |
| WO | 2007/141985 | 12/2007 |
| WO | 2010/109064 | 9/2010 |
| WO | 2017/089224 | 6/2017 |
| WO | 2018046749 A1 | 3/2018 |
| WO | 2018046750 A1 | 3/2018 |

OTHER PUBLICATIONS

Office Action in related Japanese Patent Application No. 2019-507337 dated Apr. 27, 2021, 2 pages.
Directives, Official Journal of the European Union, dated Dec. 5, 2013, 73 pages.
Opposition filing in related European Patent Application No. 17776950.2 dated Nov. 23, 2021, 30 pages.
Notice of Reasons for Refusal mailed May 11, 2021 in connection with Japanese Patent Application No. 2019-507337, 4 pgs.
Notice of Reasons for Refusal mailed Mar. 30, 2021 in connection with Japanese Patent Application No. 2019-513779, 4 pgs.
Notice of Reasons for Refusal mailed Feb. 28, 2023 in connection with Japanese Patent Application No. 2022-063795, 4 pgs.
Office Action mailed Aug. 21, 2023 in connection with Canadian Patent Application No. 3036399, 4 pgs.
Office Action mailed Aug. 22, 2023 in connection with Canadian Patent Application No. 3035297, 3 pgs.
First Office Action mailed Dec. 21, 2021 in connection with Chinese Patent Application No. 201780050839.8, 15 pgs. (including translation).
Second Office Action mailed Jun. 9, 2022 in connection with Chinese Patent Application No. 201780050839.8, 12 pgs. (including translation).
Third Office Action mailed Apr. 1, 2023 in connection with Chinese Patent Application No. 201780050839.8, 9 pgs. (including translation).
First Office Action mailed Nov. 24, 2022 in connection with Chinese Patent Application No. 201780055203.2, 15 pgs. (including translation).
Second Office Action mailed Aug. 12, 2023 in connection with Chinese Patent Application No. 201780055203.2, 19 pgs. (including translation).
International Search Report and Written Opinion mailed Nov. 30, 2017 in connection with International Patent Application No. PCT/EP2017/072840, 7 pgs.
International Search Report and Written Opinion mailed Nov. 30, 2017 in connection with International Patent Application No. PCT/EP2017/072839, 6 pgs.

* cited by examiner

SYSTEM AND METHOD FOR PROVIDING IMAGING PARAMETERS

RELATED APPLICATIONS

This application is a national phase of International Patent Application No. PCT/EP2017/072839 filed Sep. 12, 2017, which claims priority to German Patent Application No. 10 2016 117 051.8 filed Sep. 12, 2016—the contents of both of which are incorporated herein by reference.

FIELD OF THE INVENTION

The invention relates to a system with a radiographic device, for recording an X-ray image on a storage film, and with a readout device for the storage film.

BACKGROUND OF THE INVENTION

Such systems are used nowadays in X-ray technology, for instance in dental medicine, for recording X-ray images. For the purpose of storing the X-ray image, the storage film exhibits a phosphor material which has been embedded in a transparent matrix. As a result, storage centers arise which can be brought into excited metastable states by incident X-radiation. If such a storage film is exposed in an X-ray apparatus—for the purpose of imaging a bite-wing of a patient, for instance—the storage film contains a latent X-ray image in the form of excited and unexcited storage centers.

For the purpose of readout of the storage film, the latter is scanned, point-by-point, with readout light in a readout device, for instance a scanning device, as a result of which the metastable states of the excited storage centers are brought into a state that relaxes, emitting fluorescent light. This fluorescent light is registered with the aid of a detector unit, so that the X-ray image becomes visible with appropriate evaluation electronics.

In medicine, an unambiguous tracking and assignment of the storage films is extremely important. For this purpose, identification systems are employed here, as also in many other logistic fields.

SUMMARY OF THE INVENTION

It is an object of the invention to specify a system and a method, for providing information for a readout device, that is easy to operate, reliable and inexpensive.

Furthermore, it is of interest to make the process of readout of the storage film efficient and accurate.

This object may be achieved by a system having a radiographic device for recording an x-ray image on a storage film and a readout device for the storage film, wherein the storage film exhibits a data-carrier and the radiographic device and/or the readout device include(s) a data device with a read/write device for writing imaging parameters relating to the x-ray picture to the data carrier, and for reading information stored on the data-carrier, wherein the read/write device has been set up to transmit the information that has been read to the readout device, so that the imaging parameters used at the time of the recording of the x-ray image are available to the readout device for a readout of the storage film. This object may also be achieved by a storage film. This object may also be achieved by a method wherein a process of exposure of a storage film is carried out by means of a radiographic device, information that characterizes the exposure process is written to a data-carrier which his permanently assigned to the storage film, the data-carrier is readout, and the storage film is readout taking into consideration the result of the readout of the data-carrier.

The system according to the invention exhibits a radiographic device, for recording an X-ray image on a storage film, and a readout device for the storage film. In accordance with the invention, there is provision that the storage film exhibits a data-carrier. Furthermore, there is provision that the radiographic device and/or the readout device include(s) a data device with a read/write device for writing imaging parameters relating to the X-ray picture to the data-carrier, and for reading information stored on the data-carrier, said read/write device having been set up to transmit the information that has been read to the readout device, so that the imaging parameters used at the time of the recording of the X-ray image are available to the readout device for a readout of the storage film. With the system according to the invention, it is consequently possible to take appropriate information from the data-carrier for a recording of an X-ray image with the storage film. In this connection, it may be a question, for instance, of imaging parameters that are to be used for the imaging with the X-ray instrument. Furthermore, by means of the information to be read out, the number of uses of the storage film can be registered, in order to be able to calculate or estimate a presumable wear of the storage film. For instance, the information located on the data-carrier is available to the readout device for the storage film already prior to the readout process, and the readout of the storage film can, for instance, already be adapted to the imaging parameters that were used at the time of the recording of the X-ray image. A particular advantage results from the fact that the writing of the imaging parameters can be carried out by a data device of the radiographic device. This enables an extensive automation of the process of writing to the storage film, with the corresponding advantages such as a low error-rate and an extensive confidentiality of possibly sensitive data.

In one embodiment of the system, there may be provision that the information represents an identification code uniquely identifying the storage film. Consequently the storage film can be uniquely identified by a readout of the information stored onto the data-carrier. This enables a storage-film-specific linking of data acquired elsewhere, such as, for instance, the generation and/or acquisition of wear data. Furthermore, data pertaining to the storage film, linked to the identification and stored elsewhere, can also, for instance, be linked with the unique identification or with the X-ray image stored on the storage film. Information stored additionally on the data-carrier—such as, for instance, imaging parameters, wear data or the like—can also be linked with the unique identification.

In a particularly preferred embodiment, there may be provision that the data device includes a read/write device for writing imaging parameters relating to the X-ray picture to the data-carrier. By means of the read/write device, it is possible to record a picture of an X-ray image with the storage film, and to store the imaging parameters used in this process onto the data-carrier associated with the storage medium. Simultaneously or alternatively, the imaging parameters located on the data-carrier can be read out by the read/write device. Consequently a transfer of information that is independent of a central processing of information is possible solely via the data-carrier connected to the storage film. On the one hand, this secures the continuous tracking of the imaging parameters associated with the recording of the X-ray image on the storage film. On the other hand, a permanent central connection of the system to a database or the like can be dispensed with.

There may be provision, in addition, that the radiographic device has been set up to transmit the imaging parameters to the read/write device. Consequently, the imaging parameters used at the time of recording the X-ray picture can be stored directly onto the data-carrier.

The imaging parameters may be, for instance, a voltage, a current intensity, an exposure-time, a dose, a dose-area product, an f-number, data relating to a patient and/or data relating to an order. The recording of the stated imaging parameters represents a link between the stated parameters and the X-ray image located on the storage film, and consequently permits a tracking of the X-ray picture without a centralized data infrastructure having to be made available.

In a particularly preferred embodiment, there is provision that the data-carrier is an RFID transponder. Accordingly there may be provision that the read/write device is an RFID read/write device. The RFID-based connection technology may, for instance, operate in accordance with standard ISO/IEC 18000-x, but is not restricted to this standard.

The storage film according to the invention is designed for such a system and exhibits a light-sensitive layer, in particular for the storage of an X-ray image, and is designed to be kept in a light-shielding sheath. There is provision that the storage film exhibits a data-carrier that is designed to store imaging parameters of an X-ray picture and to make them available for a readout. Consequently the advantages already elucidated above arise.

The method according to the invention for providing information for a readout device has the following steps. A process of exposure of a storage film is carried out by means of a radiographic device, so that an X-ray image arises on the storage film. The imaging parameters used at the time of recording the X-ray picture are written on the data-carrier permanently assigned to the storage film. The data-carrier is read out. The storage film is read out, taking into consideration the result of the readout of the data-carrier. Prior to or after the exposure, a marking of the storage film characterizing the storage film can be read from the data-carrier. Consequently the imaging parameters used at the time of recording an X-ray picture can be stored on the data-carrier and, for instance, can be read out and used at the time of the readout of the storage film or at the time of an interpretation of the X-ray image located on the storage film, without a centralized flow of data having to take place. In this case, the step of writing to the data-carrier includes the storing of information that characterizes the exposure process. In this case, it may—as already mentioned—be a question, for instance, of the imaging parameters at the time of recording the X-ray picture. The readout of the storage film takes into consideration the result of the readout of the data-carrier. If, for instance, the imaging parameters with which the X-ray image was exposed onto the storage film are taken into consideration at the time of the readout of the storage film, under certain circumstances the readout conditions for the storage film can be optimized. In this connection it is relevant that the X-ray device stores the imaging parameters directly into the data-carrier of the storage film by means of the data device. Consequently no manual inputs are required, and a high degree of security arises with respect to the correctness of the information stored on the data-carrier. Accordingly, intentional or unintentional incorrect inputs can be avoided. At the same time, the entire sequence of operations is temporally shortened and improved as regards security in comparison with the case in which, for instance, manual inputs would have to be performed. The advantages of a decentralized storage present themselves at the same time: rapid availability of the data, no elaborate connection to a central system, etc.

BRIEF DESCRIPTION OF THE DRAWINGS

The invention will now be elucidated in more detail with reference to the appended drawings. Shown are.

DETAILED DESCRIPTION OF THE INVENTION

Figure 1A:
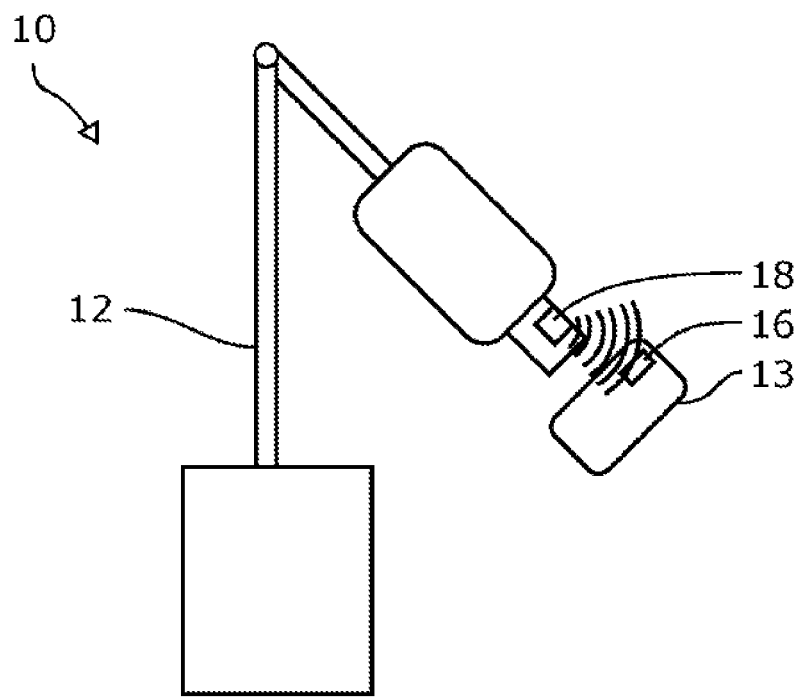
FIGS. 1A, 1B in schematic representation, parts of a system according to the invention.
Figure 1B:
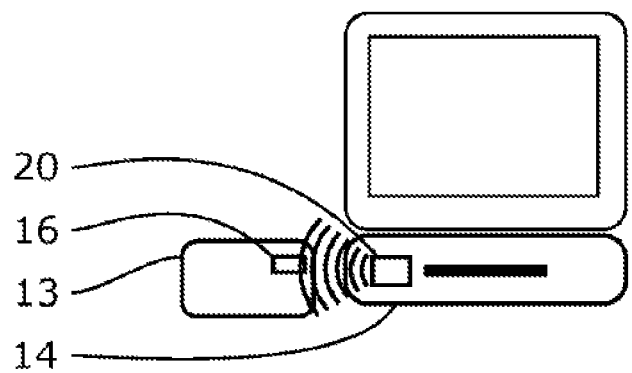

A system 10 for providing information is represented in FIGS. 1A and 1B. The system 10 comprises a radiographic device 12 (FIG. 1A) for exposing a storage film 13 with an X-ray image—such as is employed in dental medicine, for instance—and also a readout device 14 for readout of the X-ray image located on the storage film 13. For the purpose of recording an X-ray image, the storage film 13 is ordinarily arranged at a suitable location in the oral cavity of a patient by means of holding devices which are not represented, and is exposed with the aid of the radiographic device 12. For the exposure, suitable imaging parameters have to be set on the radiographic device 12 for the respective recording situation. These imaging parameters include, for instance, a voltage, a current intensity, an exposure-time, a dose, a dose-area product and/or an f-number, and so determine the recording conditions. But patient-specific or order-specific information may also be found amongst the imaging parameters.

In addition to the actual X-ray-sensitive structure, the storage film 13 includes an RFID transponder 16. The RFID transponder 16 may have been arranged, for instance, on or in a light-tight protective sheath which is ordinarily provided. The RFID transponder 16 cooperates with a read/write device 18 on the radiographic device 12 and with a reader 20 on the readout device 14.

The read/write device 18 provided on the radiographic device 12 is designed to write some or all of the imaging parameters to the RFID transponder 13. For this purpose, the desired values set prior to the exposure process, and/or measured values acquired during or after the exposure process, can, for instance, be acquired as imaging parameters and written to the RFID transponder 16. In addition, the read/write device 18 can also read out information located on the RFID transponder. For instance, information relating to, for instance, the patient, the order, the X-ray system and/or the overall system, or similar information, can be stored on the RFID transponder 16 already at the time of preparation of the X-ray picture on the storage film, and can then be read out by the radiographic device 12 and, where appropriate, may find application in the configuration of the process of exposure of the storage film 13.

The writing of the information to the RFID transponder 13 by the radiographic device 12 by means of the read/write device 18 may also include the writing of the imaging parameters actually used, and/or the writing of measured values. The writing can be undertaken automatically at the end of an imaging process, independently of an operating process.

After the exposure has been undertaken, the X-ray image located on the storage film 13 has to be read out. In the embodiment of the system 10 that is shown, the readout device 14 is provided for this purpose. The readout device 14 may be, for instance, a scanning device which, by means of a guided laser beam, activates the metastable states in the storage-film matrix and in this way enables a readout of the X-ray image. The imaging parameters contained in the RFID transponder 16 can be read out by means of the reader 20 provided on the readout device 14, for instance already prior to the process for readout of the storage film 13, and can, where appropriate, be used for the readout/scanning process. Knowledge of the imaging parameters may, under certain circumstances, facilitate the setting of the readout process.

The reader 20 provided in the readout device 14 may also have been realized as a read/write device similar to read/write device 18. In this way, information still located on the RFID transponder 16 after the readout of the storage film 13 can be deleted. Alternatively or additionally, some or all of the readout results can be written again to the RFID transponder 16 and stored in this way. A note may also be placed on the RFID transponder 16, which indicates that the storage film 13 has already been read out.

Figure 2A:
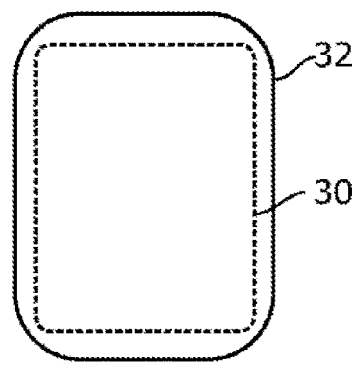
FIGS. 2A-D in schematic representation, various embodiments of a storage film according to the invention.

FIGS. 2A-D show an embodiment of a storage film 30. The storage film 30 has, as shown in FIG. 2A, been inserted in a protective sheath 32 during its handling. The protective sheath 32 serves as a mechanical protection, in order to protect the sensitive storage film 30 against scratching or kinking. At the same time, the protective sheath 32 protects the storage film 30 against undesirable incidence of light, which would destroy the latent stored image located on the storage film 30 or would undesirably expose a yet unexposed storage film. For a readout, the storage film 30 has to be taken out of the protective sheath in a protected environment and is scanned, point-by-point or line-by-line, with a readout light, as a result of which the metastable states, storing the X-ray image, of the excited storage centers relax and emit fluorescent light.

Figure 3:
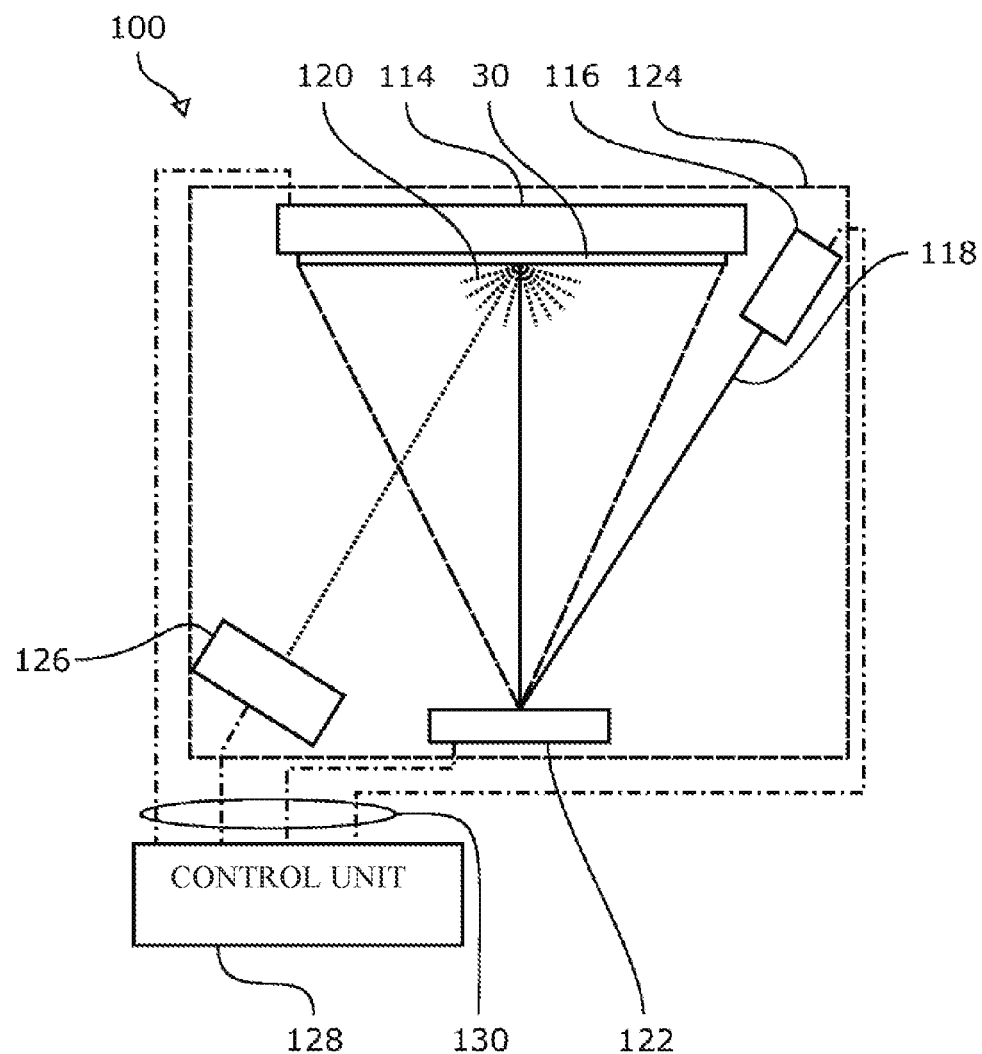
FIG. 3 in a schematic representation, an embodiment of a scanning device.

FIG. 3 shows a scanning device 100 for readout of such a storage film 30 which in the form of metastable storage centers excited by X-radiation bears a latent X-ray image.

The scanning device 100 exhibits a support device 114 for the storage film 30. For instance, the storage film 30 may have been attached to the support device 114 by underpressure in such a way that the storage film 30, which is generally flexible, presses close and flat against the support surface 114.

The scanning device 100 further includes, as source of readout light, a laser 116 which generates a readout-light beam 118 having a wavelength in the red, with which the metastable storage centers of the storage film 30 can be excited to fluoresce. This fluorescent light 120 typically lies in the blue.

In the present embodiment of the scanning device 100, the laser 116 has been arranged in such a way that it directs the readout-light beam 118 onto a controllable deflection unit. In the present case, the controllable deflection unit takes the form of a mirror 122. But other deflection units besides mirrors are also conceivable, such as lens systems or the like. The mirror 122 may have been realized as a micromirror, in particular as a MEMS component, and in this way may enable a scanning of the surface of the storage film 30 without, or with only little, relative motion between the mirror 122 and the support device 114. Alternatively, the mirror 122 may also have been provided conventionally as a rotating mirror for a drum scanner. In this case, a relative motion between the support device 114 and the mirror 122 has been realized by means of a transport device (not illustrated).

The scanning device 100 may further include a reflector 124, indicated in the drawing by dashed lines, which encloses the entire measuring space around the storage film 30 in light-tight manner, so that the fluorescent light 120 emanating from the storage film is reflected to a photodetector 126. In order to prevent scattered readout light 118 from getting into the photodetector 126, suitable measures—such as, for instance, a dichroic filter material—may have been provided.

For the purpose of controlling the readout process, the scanning device 100 includes a control unit 128 which, for instance, in addition to the control function may also carry out evaluating or correcting functions. But the control unit 128 itself or the evaluating and/or correcting functions may also have been implemented on a separate computer. The control unit 128 is connected to the support device 114, to the detector 126, to the laser 116 and also to the mirror 122 by means of lines 130.

For the purpose of readout, the control unit 128 drives the laser 116 and also the mirror 122 and scans the storage film 30 sequentially, point-by-point, with the readout-light beam 118. In this process, the intensity of the emitted fluorescent light 120 is registered with the aid of the photodetector 126 and prepared for output in the control unit 128.

Figure 2B:
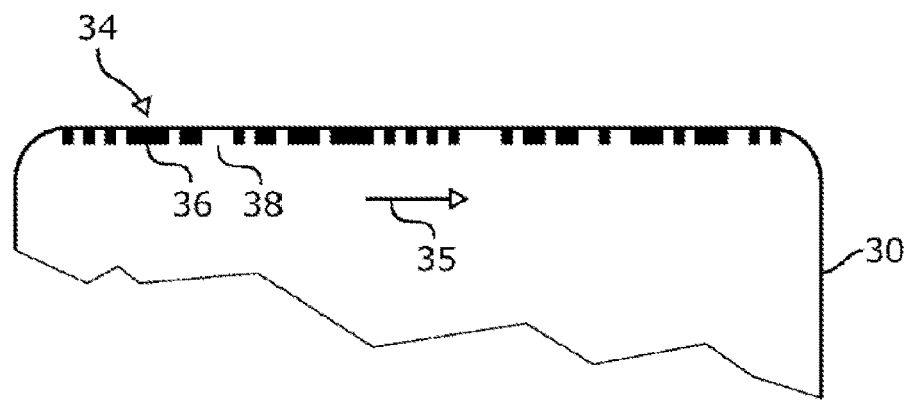
Figure 2C:
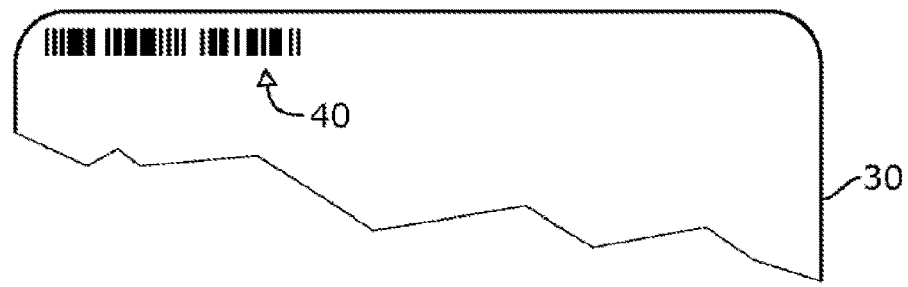
Figure 2D:
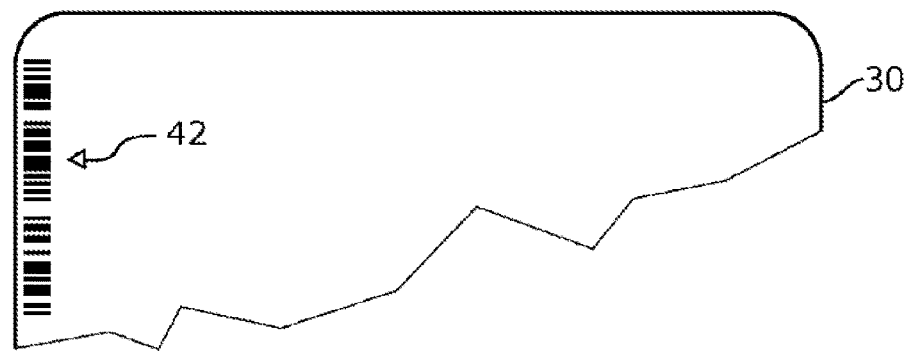

In FIGS. 2B-D three different embodiments of a storage film 30 are represented. The storage film 30 represented in FIG. 2B exhibits on its upper edge a barcode structure 34 which substantially covers the complete width of the storage film 30 in the direction 35 of a scan line. The barcode structure 34 is designed in such a way that, at the time of a readout of the storage film, such as, for instance, with the scanning device 100, it exhibits, in the scanning direction of the readout-light beam 118, regions 36 of increased reflectivity for the readout-light beam 118 and regions 38 of lower reflectivity, for instance with normal reflectivity. The regions 36 of increased reflectivity can act, for instance, as scattering regions. At the time of a scanning of the storage film, the scattered light arising from the barcode structure 34 at the time of a line-by-line scanning can consequently be detected, for instance prior to a normal readout process. Since in this process a high local resolution is of no importance, the scattered light can, for instance, be registered with a simple photodiode (not illustrated). Alternatively or additionally, the photodetector 1126 which is present anyway may also possibly undertake this task, given the low sensitivity that is demanded.

FIGS. 2C and D show modifications. In contrast to the barcode structure of FIG. 2B, barcode structure 40 covers only a part of the surface of the storage film 30 in the scanning direction 35. In the modification shown in FIG. 2D, a barcode structure 42 extends perpendicular to the line-by-line scanning direction 35 and consequently requires a detection of the scattered light arising at the start of each scan line.

Figure 4:
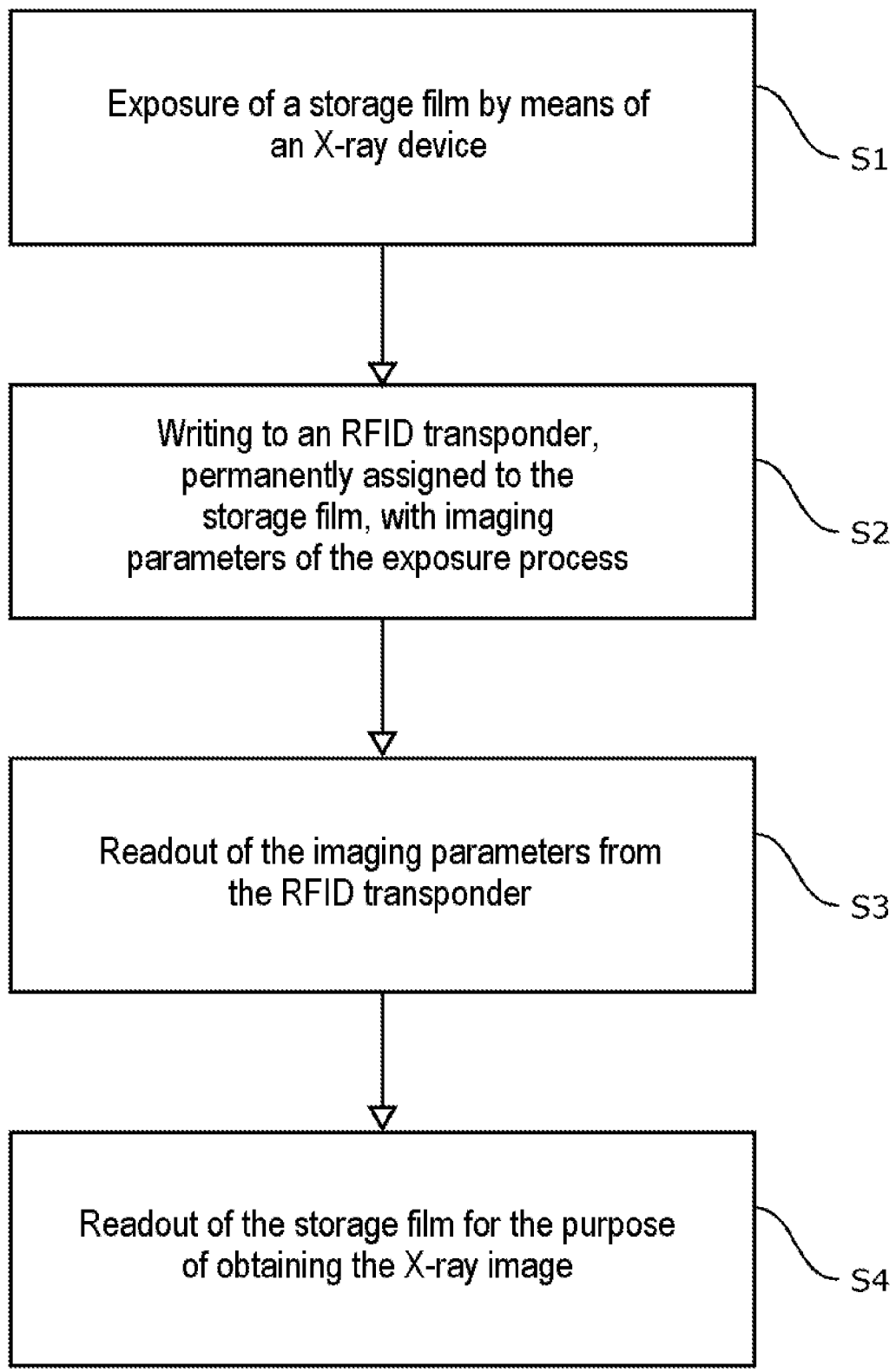
FIG. 4 a flowchart of a method according to the invention.

FIG. 4 describes an embodiment of a method for providing information for a readout device. The method comprises the following steps:

A storage film is exposed (S1) by means of an X-ray device. In the course of the exposure process an X-ray image is generated latently in the storage film.

An RFID transponder permanently assigned to the storage film is written to (S2) with imaging parameters of the exposure process. The process of writing (S2) may take place already prior to the step of exposure (S1) if exclusively desired values to be set are to be saved on the RFID transponder. Alternatively or additionally, the process of writing (S2) may take place during or after the exposure process (S1), and, alternatively or additionally, measured values acquired during the exposure process (S1) can be stored onto the RFID transponder. For the writing to the RFID transponder, the storage film may remain in the X-ray device or may have already been taken out of the X-ray device.

The imaging parameters located on the RFID transponder are read out (S3). After the end of the exposure process (S1) and after the writing to the RFID transponder (S2), the storage film can be taken to a readout device, in order to read out the imaging parameters therein.

The X-ray image located on the storage film is read out (S4) by means of a suitable readout device. It may be a question, for instance, of a scanning device which activates the latent X-ray image by means of a laser and in this way enables a readout. The steps of the readout of the imaging parameters (S3) and of the readout of the storage film (S4) can be undertaken independently of one another. Prior to the readout of the storage film (S4), the imaging parameters are read out (S3) from the RFID transponder, in order to obtain inferences from the imaging parameters as to suitable settings for the readout of the storage film.

What is claimed is:

1. A system comprising:
   a storage film having a data-carrier;
   a radiographic device configured to record an X-ray image on the storage film; and
   a readout device configured to read the storage film; wherein
   the radiographic device includes a first read/write device configured to write desired exposure values and/or measured exposure values used at a time of an exposure of the X-ray image recorded on the storage film to the data-carrier without any manual input,
   the readout device includes a second read/write device configured to read the desired exposure values and/or the measured exposure values from the data-carrier so that the desired exposure values and/or the measured exposure values used at the time of the exposure of the X-ray image are utilized by the readout device for a readout of the storage film.

2. The system as claimed in claim 1, wherein the first read/write device is further configured to write information, and the second read/write device is further configured to read the information, and wherein the information represents an identification code uniquely identifying the storage film.

3. The system as claimed in claim 1, wherein the radiographic device is configured to transmit the desired exposure values and/or the measured exposure values to the first read/write device.

4. The system as claimed in claim 1, wherein the desired exposure values and/or the measured exposure values comprising one or more of a dose, a dose-area product, an f-number, data relating to a patient or data relating to an order is also written to the data-carrier by the first read/write device.

5. The system as claimed in claim 1, wherein the data-carrier comprises an RFID transponder.

6. The system as claimed in claim 1, wherein the storage film exhibits an optically-readable marking, and the second read/write device has been set up to acquire the optically-readable marking.

7. The system as claimed in claim 6, wherein the optically-readable marking comprises a barcode or a QR code.

8. The system as claimed in claim 1, wherein the desired exposure values and/or the measured exposure values are for one or more of a voltage, a current intensity, or an exposure-time.

9. A method for providing information for a readout device, comprising the following steps:
   performing an exposure process of a storage film with a radiographic device configured to record on the storage film;
   writing desired exposure values and/or measured exposure values acquired during the exposure process to a data-carrier without any manual input, the data-carrier being permanently assigned to the storage film;
   reading out the data-carrier; and
   reading out the storage film using the desired exposure values and/or the measured exposure values written on the data-carrier.

10. The method as claimed in claim 9, wherein the desired exposure values and/or the measured exposure values are for one or more of a voltage, a current intensity, or an exposure-time.

* * * * *